United States Patent [19]

Sato et al.

[11] 4,011,247

[45] Mar. 8, 1977

[54] METHOD FOR THE PREPARATION OF AN ORGANOHYDROGENPOLYSILOXANE AS A PRODUCT OF A PARTIAL ADDITION REACTION

[75] Inventors: Yasuhiko Sato; Hiroshi Inomata; Toshio Shiobara, all of Annaka, Japan

[73] Assignee: Shinetsu Chemical Company, Tokyo, Japan

[22] Filed: Oct. 4, 1974

[21] Appl. No.: 512,369

[30] Foreign Application Priority Data

Oct. 8, 1973    Japan ............................ 48-113047

[52] U.S. Cl. .................... 260/348 SC; 260/46.5 G; 260/46.5 H; 260/448.2 E; 260/448.2 H

[51] Int. Cl.$^2$ ....................................... C07D 301/00

[58] Field of Search .............. 260/348, 46.5, 448.2, 260/348 SC, 448.2 E, 448.2 H

[56] References Cited

UNITED STATES PATENTS

| | | | |
|---|---|---|---|
| 2,970,150 | 1/1961 | Bailey | 260/348 SC |
| 3,663,181 | 2/1972 | Shannon | 252/472 |
| 3,666,813 | 5/1972 | Hindin et al. | 252/472 |

*Primary Examiner*—John D. Randolph
*Attorney, Agent, or Firm*—Toren, McGeady and Stanger

[57] ABSTRACT

Starting from an organohydrogenpolysiloxane having at least two hydrogen atoms directly bonded to the silicone atoms, an organohydrogenpolysiloxane is obtained in which part of the silicon-bonded hydrogen atoms have been converted into organic groups and the remaining silicon-bonded hydrogen atoms are left unreacted. The starting organohydrogenpolysiloxane is brought to the partial addition reaction with less than equivalent amount of an organic unsaturated compound having aliphatic double bond in the molecule in the presence of a platinum catalyst, and the reaction mixture is subjected to distillation while the platinum catalyst is deactivated by added benzothiazole or derivatives thereof, thus providing for the production of the organohydrogenpolysiloxane of the invention in reproducibly in high yield. The compounds are useful as crosslinking agents in the manufacture of various silicone products.

6 Claims, No Drawings

METHOD FOR THE PREPARATION OF AN ORGANOHYDROGENPOLYSILOXANE AS A PRODUCT OF A PARTIAL ADDITION REACTION

FIELD OF THE INVENTION

This invention relates to a novel method for the preparation of an organohydrogenpolysiloxane with a relatively low molecular weight by a partial addition reaction to leave some unreacted silicon-bonded hydrogen atoms and, in particular, to a method for the preparation of an organohydrogenpolysiloxane in reproducibly high yield by the partial addition reaction, in the presence of a platinum catalyst, between an organohydrogenpolysiloxane with relatively low molecular weight, having at least two silicon-bonded hyrdogen atoms in a molecule and an organic unsaturated compound with an aliphatic double bond in the molecule as the starting material to leave part of the silicon-bonded hydrogen atoms unreacted.

DESCRIPTION OF THE PRIOR ART

In silicone chemistry, one of the most prevailing and very important means for the preparation of organopolysiloxanes modified with various kinds of organic groups bonded through Si-C linkages is the method of the addition reaction in the presence of a platinum catalyst between an organohydrogenpolysiloxane with silicon-bonded hydrogen atom or atoms and an organic unsaturated compound with aliphatic unsaturation.

The platinum catalyst employed in the above reaction is so reactive against the Si-H linkages that the addition reaction can proceed even under moderate conditions efficiently. It causes, on the other hand, several disadvantages when the desired reaction product is an organohydrogenpolysiloxane with silicon-bonded hydrogen atom or atoms left unreacted by the partial addition reaction on part of the silicon-bonded hydrogen atoms originally present in the starting organohydrogenpolysiloxane.

For example, a viscosity increase of the reaction mixture often occurs in the processing after the reaction, i.e., in the stripping of the solvent and the unreacted materials and in the distillation to separate the by-products, leading to the increase in the amount of the high-boiling, undistillable residue and to a decrease in the yield of the desired product. In some cases, even complete gelation of the reaction mixture takes place resulting in no recovery of the reaction product.

Therefore it is difficult to obtain high yields in the preparation of the organohydrogenpolysiloxanes as the products of the partial addition reaction by the above method, and even more difficult to expect reproducible results even when the desired siloxane can be obtained with certain yields.

The mechanism of the above described undesirable phenomena is, in the opinion of the inventors of the present invention, the activation and scission of the Si-H linkages by the action of the platinum catalyst. This invention is the results of an extensive study which the inventors carried out to obtain the reaction products of the object in high yields in consideration of the possibility that the yields would be improved if the platinum catalyst can be deactivated in the distillation step after completion of the reaction.

OBJECTS OF THE INVENTION

Accordingly, it is a general object of the invention to provide a method of producing organopolysiloxanes having a relatively low molecular weight with part of the Si-H linkages left unreacted by the partial addition reaction.

It is a further object of the invention to provide a method of producing such organopolysiloxanes in a constantly high yield.

SUMMARY OF THE INVENTION

The method of the present invention for the preparation of an organohydrogenpolysiloxane comprises the steps of:

A. the partial addition reaction between
  a. a cyclic or non-cyclic organic unsaturated compound with an aliphatic double bond in the molecule and
  b. a starting organohydrogenpolysiloxane represented by the average formula $$(R)_a(H)_b SiO_{(4-a-b)/2}$$

where R is the same or different monovalent organic group, a and b are each positive numbers expressed as $1 \leq a \leq 2$ and $b \leq 1$, respectively, with the proviso that $2 \leq (a+b) \leq 3$, and having at least two hydrogen atoms directly bonded to the silicon atoms through Si-H linkages in one molecule, in an amount such that the amount of the hdrogen atoms in the starting organohydrogenpolysiloxane is in equimolar excess over to the aliphatic double bond contained in compound (a), in the presence of a platinum catalyst, by which part of the Si-H linkages are subjected to the addition reaction with the aliphatic double bonds and the remaining of the Si-H linkages left unreacted, B. addition of benzothiazole or a derivative thereof to the reaction mixture obtained by the partial addition reaction in an amount larger than equimolar to the platinum catalyst, and C. recovery of the organohydrogenpolysiloxane of the object by distillation.

The method of the present invention is advantageous for the preparation of the desired organohydrogenpolysiloxanes in high yields without such undesirable troubles as the gelation of the reaction mixture.

DESCRIPTION OF THE PREFERRED EMBODIMENT

To describe the invention in further detail, the starting organohydrogenpolysiloxanes are represented by the above-mentioned average formula and contain at least two hydrogen atoms directly bonded to the silicon atoms through Si-H linkages in one molecule and they are exemplified by the following compounds.

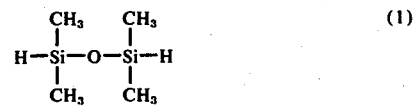

(1)

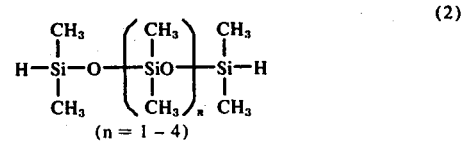

(2)

-continued

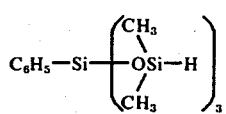
(3)

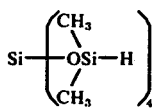
(4)

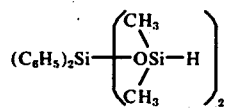
(5)

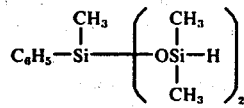
(6)

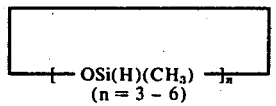
(7)

$\quad(n = 3 - 6)$

The organic unsaturated compounds on one side employed in the method are cyclic or non-cyclic unsaturated compounds with an aliphatic double bond in the molecule and their molecular weights are preferably lower than 150. They are exemplified by ethylene, propylene, cyclohexene, styrene, α-methylstyrene, methyl acrylate, ethyl acrylate, methyl methacrylate, ethyl methacrylate, allyl acetate, allyl acrylate, allyl methacrylate, allyl glycidyl ether, vinyl cyclohexene monoepoxide and 4-vinyl styreneoxide.

In the method of the present invention where the starting organohydrogenpolysiloxane and the organic unsaturated compound are subjected to the addition reaction in the presence of a known platinum catalyst, the molar ratio of the former to the latter is such that the molar amount of the silicon-bonded hydrogen atoms in the former is larger than the molar amount of the aliphatic double bonds in the latter. In an embodiment of the process of the present invention, it is naturally possible to leave some of the silicon-bonded hydrogen atoms unreacted by suppressing or stopping the reaction at certain low degree of reaction even when the amount of the aliphatic double bonds is equimolar to the silicon-bonded hydrogen atoms or more. Such a process is, however, never recommended in industrial production because of the difficulty in the controlling of the reaction, the increase in the numbers of by-products and the economical disadvantages.

The platinum catalyst employed in the method of the present invention is a conventional one exemplified by chloroplatinic acid, adducts of chloroplatinic acid with alcohols, complexes of chloroplatinic acid with olefins, platinum black or finely dispersed platinum supported on alumina or silica carriers. Chloroplatinic acid or its complexes with olefins mentioned above are preferably employed as solutions in a suitable solvent, such as, alcohols, ketones, ethers and hydrocarbons. The platinum catalysts in solid state must be dispersed as finely as possible and the carriers to support the platinum catalyst must have specific surfaces which are as large as possible.

Various kinds of inert organic solvents may be employed as the reaction medium for the addition reaction in the method of the present invention. Suitable solvents for use as the reaction medium are, for example, hexane, heptane, benzene, toluene, xylene, mineral spirit, ethyl ether and propyl ether.

The amount of the platinum catalyst is in the range from $10^{-7}$ mole to $10^{-3}$ mole per mole of the aliphatic double bonds in the organic unsaturated compound. Lower reaction temperatures, for example, below 150° C, or more preferably below 110° C, are preferred so long as the reaction takes place with sufficient velocity. When the organic unsaturated compound is itself readily polymerizable, a polymerization inhibitor, such as, 2,6-di-tert-butyl-4-methylphenol is added in the reaction mixture.

When the partial addition reaction has been completed as described above, benzothiazole or derivatives thereof are added into the reaction mixture. Benzothiazole and several of its derivatives suitable in the method of the present invention are shown below by their structural formulas including 2-benzothiazole disulfide which is the most preferred one.

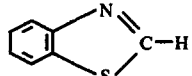
(1)

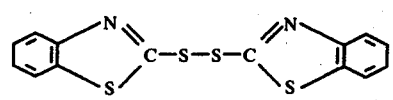
(2)

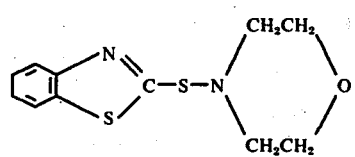
(3)

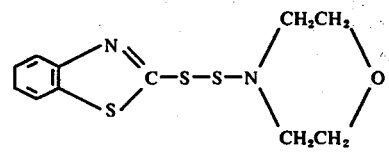
(4)

The amount of benzothiazole or derivatives thereof to be added to the reaction mixture is necessarily more than an equimolar amount to the amount of the platinum catalyst employed in the addition reaction. It is a general practice in the case where the platinum catalyst is dissolved homogeneously in the reaction mixture to use about 20 to 200 moles or more of the compound per mole of the platinum catalyst and a higher amount of the benzothiazole compound is disadvantageous from the standpoint of economy as well as its bad smell and coloring in the reaction mixture.

The distillation of the reaction mixture wherein the benzothiazole compound has been added is carried out in a conventional manner, for example, under reduced pressure and is not critical in itself. The benzothiazole compounds are not so readily distilled from the reaction mixture because of their relatively high boiling points. In no occasion gelation of the reaction mixture takes place during the distillation and the yield of the organohydrogenpolysiloxane of the object is very good. In some cases for the application of the organohydrogenpolysiloxane, the reaction mixture itself may be employed after the stripping of the solvent and the unreacted starting materials without further distillation into individual reaction products, although, in such cases, the benzothiazle compound added before the with the addition of the individual benzothiazole compounds as shown in the following table. Other data are also shown in the table.

|  | Experiment No. 1 | Experiment No. 2 | Experiment No. 3 | Experiment No. 4 |
| --- | --- | --- | --- | --- |
| Additive | 2-(4-Morpho-dinyl-dithio)-benzothiazole | None | Quinoline | Benzothiazole |
| Amount of Additives, g | 0.0167 | — | 0.0131 | 0.1188 |
| Reaction mixture taken, g | 33.3 | 27 | 23.3 | 30.0 |
| Addition product obtained, g | 15.8 | 0 | 2.9 | 5.9 |
| State of the residue in distillation | Liquid of low viscosity | Gelled mass | Gelled mass | Gelled mass | addition reaction still remains in the reaction mixture must be removed by some means such as adsorption by active charcoal.

With respect to the application of the organohydrogenpolysiloxanes obtained by the method of the present invention, they are as useful as the conventional organohydrogenpolysiloxanes of other types as the crosslinking agent in the manufacturing of various kinds of silicone products which are cured by the addition type crosslinking mechanisms. They are also useful as the crosslinking agent in the silicon products of the condensation curing types by converting the Si—H bond into Si—OH bond by hydrolyzing it under mild conditions in the presence of alkalis.

Folloiwing are the examples of the present invention.

EXAMPLE 1.

Into a 500 ml-volume three neck flask equipped with a thermometer, a stirrer and a reflux condenser, were taken 159.8g of 1,3,4,7-tetramethylcyclotetrasiloxane, 41.3 g of vinylcyclohexene monoepoxide, 120 g of toluene and 0.2 g of a solution of ethylene platinous chloride in benzene containing 0.5% of platinum as metal, and the reaction mixture was subjected to reaction by heating at 92° C for 5 hours with agitation. After completion of the reaction, the reaction mixture was distilled with 0.24 g of 2-(4-morpholinyl-dithio)-benzothiazole added to give 66.3 g of a fraction with a boiling point of 110° C/1.5-2 mmHg, density 1.060, viscosity 8.5 centistokes at 25° C and refractive index 1.4430 at 25° C. The fraction was identified to be the organohydrogenpolysiloxane expressed by the structural formula below.

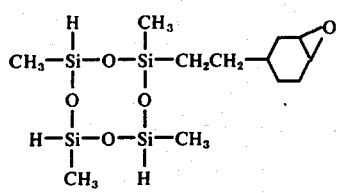

EXAMPLE 2.

The reaction mixture after completion of the addition reaction carried out in the same manner as in Example 1 was stripped of the solvent and the unreacted starting materials and divided into four portions, each of which was subjected to distillation without or As is seen in the table, the distillation of the reaction mixture was almost impossible without the addition of the benzothiazole compound (Experiment No. 2) or incomplete according to the nature and the amount of the benzothiazole compounds added (Experiments Nos. 3 and 4).

EXAMPLE 3.

Into a 1000 ml-volume three neck flask were taken 244.4 g of 1,3,5,7-tetramethylcyclotetrasiloxane, 100 g of α-methylstyrene, 350 g of toluene and 2.02 g of alumina-supported platinum catalyst containing 5% of platinum and the mixture was heated under reflux of toluene for 8.5 hours with agitation. The reaction mixture was then filtered and the filtrate was distilled with 0.3 g of 2-benzothiazolyl disulfide added to give 162.7 g of a fraction with a boiling point of 100°–102° C/1 mmHg, density 1.029, viscosity 3.9 centistokes at 25° C and refractive index 1.4581 at 25° C. This fraction was identified to be the organohydrogenpolysiloxane expressed by the structural formula below.

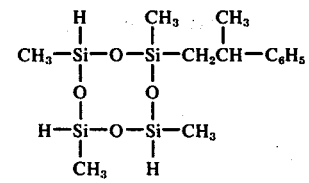

The residue left in the still after the distillation above was further subjected to distillation under reduced pressure to give 53.4 g of another fraction with the boiling point 174°–175° C/1 mmHg, density 1.044, viscosity 17.1 centistokes at 25° C and refractive index 1.4860 at 25° C, which was identified to be the organohydrogenpolysiloxane expressed by the structural formula below.

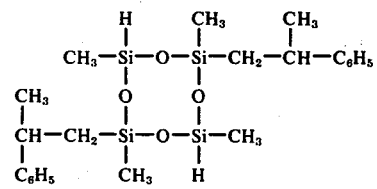

As a control, the same procedure as described above was repeated but without the addition of 2-benzothiazolyl disulfide. No reaction products were obtained by the distillation because gelation of the reaction mixture took place before a distillate came out.

EXAMPLE 4.

The reaction mixture of 24 g of 1,3,5,7-tetramethyl-cyclotetrasiloxane, 8 g of ethyl acrylate and 30 g of toluene with 0.2 g of the same platinum catalyst as employed in Example 3 and 0.2 g of 2,6-di-tertbutyl-4-methylphenol was heated under reflux of toluene for 8 hours with agitation and the catalyst was filtered off after completion of the reaction. The filtrate was subjected to distillation with 0.04 g 2-benzothiazolyl disulfide added to give 6.3 g of a fraction which was identified to be the mixture of the isomers expressed by the following structural formulas.

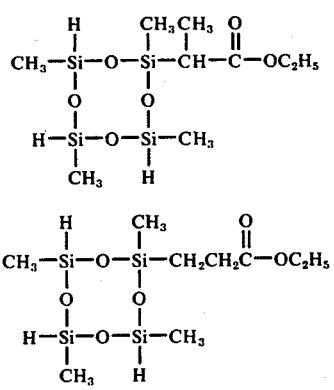

As a control, the same procedure as described above was repeated but without the addition of 2-benzothiazolyl disulfide. The distillation was unsuccessful with no distillate obtained due to the rapid viscosity increase and final gelation of the reaction mixture.

EXAMPLE 5.

The reaction mixture of 72 g of 1,3,5,7-tetramethyl-cyclotetrasiloxane, 20 g of allyl acetate and 100 g of toluene with 0.4 g of the same platinum catalyst as employed in Example 3 and 0.3g of tert-butyl-4-methylphenol was heated under reflux of toluene for 14 hours with agitation and the catalyst was filtered off after completion of the reaction. The filtrate was subjected to distillation under reduced pressure with 0.15 g of N-oxydiethylene-2-benzothiazole added. Two fractions were obtained at 95° C/1 mmHg and 115°–120° C/1 mmHg, respectively (the temperatures are those in the oil bath for heating the still), weighing 7.5 g and 22 g. They were identified to be the organohydrogenpolysiloxanes shown by the structural formulas below, respectively.

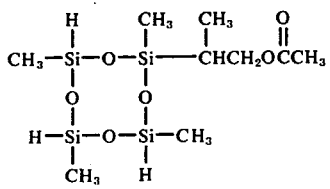

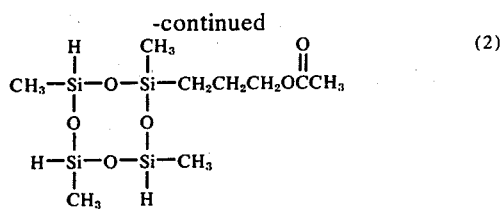

As a control, the same procedure as described above was repeated but without the addition of the 2-benzothiazolyl disulfide resulting only in the gelation of the reaction mixture before a distillate came out.

EXAMPLE 6.

The reaction mixture of 72 g of 1,3,5,7-tetramethyl-cyclotetrasiloxane, 20 g of methyl methacrylate and 100 g of toluene with 0.4 g of the same platinum catalyst as employed in Example 3 and 0.3 g of 2,6-di-tert-butyl-4-methylphenol were heated under reflux of toluene for 14 hours with agitation and the catalyst was filtered off after completion of the reaction. The filtrate was subjected to distillation under reduced pressure with 0.06 g of 2-benzothiazolyl disulfide added to give 15.4 g of the organohydrogenpolysiloxane shown by the structural formula below.

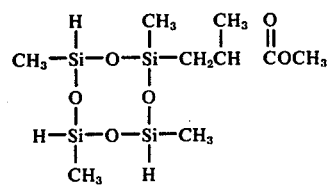

As a control, the same procedure as described above was repeated but without the addition of 2-benzothiazolyl disulfide. In this case, the distillation was impossible because of the viscosity increase and final gelation of the reaction mixture.

EXAMPLE 7.

The reaction mixture of 120 g of 1,3,5,7-tetramethyl-cyclotetrasiloxane, 38 g of allyl glycidyl ether and 230 g of toluene with 0.067 g of the same catalyst used in Example 1 was heated at 84° to 89° C for 3 hours with agitation. When the reaction was completed the reaction mixture added with 0.12 g of N-oxydiethylene-2-benzothiazole was subjected to distillation under reduced pressure to give 59.2 g of fraction which distilled out at 126°–127° C/45 mmHg. The fraction was identified to be the organohydrogenpolysiloxane of the addition product expressed by the structural formula below.

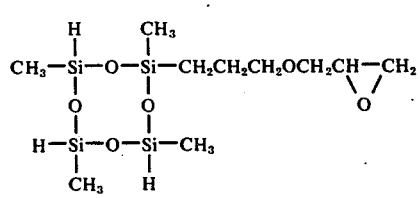

As a control, the same procedure as described above was repeated but without the addition of the N-oxydiethylene-2-benzothiazole where the distillation gave no product because of the viscosity increase and final gelation of the reaction mixture.

EXAMPLE 8.

Into the mixture of 50 g of mixed siloxanes of 1,1,3,3,5,5-hexamethyltrisiloxane and 1,1,3,3,5,5,7,7-oxtamethyltetrasiloxane, 11.4 g of α-methylstyrene and 65 g of toluene was added 0.37 g of the same platinum catalyst as employed in Example 7 and the reaction mixture was heated at 105° to 108° C for 3 hours with agitation. The reaction mixture was then subjected to distillation under reduced pressure with the addition of 0.18 g of benzothiazolyl disulfide to give 9.6 g of a fraction boiling at 103°–109° C/3 mmHg and 6.9 g of another fraction boiling at 114°–118° C/3 mmHg. They were identified to be the organohydrogenpolysiloxanes expressed by the following structural formulas, respectively.

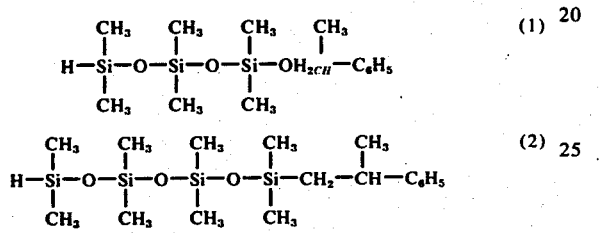

EXAMPLE 9.

Into the mixture of 54 g of 1,3,5,7,9,11-hexamethylcyclohexasiloxane, 8.9 g of α-methylstyrene and 65 g of toluene was added 0.29 g of the same platinum catalyst as employed in Example 7 and the reaction mixture was heated at 95° C for 7.5 hours with agitation. After completion of the reaction, the reaction mixture was subjected to distillation under reduced pressure with 0.14 g of 2-benzothiazolyl disulfide to give 4.2 g of a fraction boiling at 119°–123° C/1 mmHg, which was identified to be the organohydrogenpolysiloxane expressed by the structural formula below.

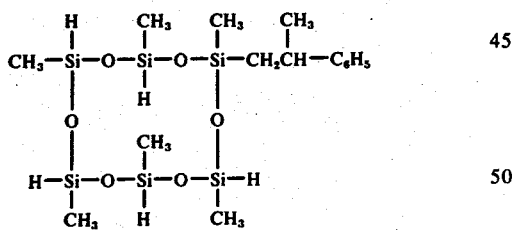

As a control, the same procedure as described above was repeated but without the addition of 2-benzothiazolyl disulfide giving no distillable product with the gelation of thereaction mixture.

EXAMPLE 10.

Into the mixture of 13.4 g of tetrakis(dimethylhydrogensiloxy)silane, 8.9 g of α-methylstyrene and 25 g of toluene was added 0.29 g of the same platinum catalyst as employed in Example 7 and the reaction mixture was heated at 83° C for 4 hours with agitation. After completion of the reaction, the reaction mixture with 0.15 g of 2-benzothiazolyl disulfide added was subjected to distillation under reduced pressure to give 2.3 g of a fraction. The fraction was identified to be the organohydrogenpolysiloxane expressed by the structural formula below.

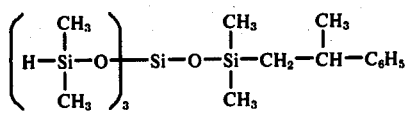

As a control, the same procedure as described above was repeated, but without the addition of 2-benzothiazolyl disulfide and produced no distillable product with the gelation of the reaction mixture.

What is claimed is:

1. A method for the preparation of an organohydrogenpolysiloxane comprising the steps of:
   A. partial addition reaction between
      a. a cyclic or non-cyclic organic unsaturated compound with an aliphatic double bond in the molecule selected from the group consisting of ethylene, propylene, cyclohexene, styrene, α-methylstyrene, methyl acrylate, ethyl acrylate, methyl methacrylate, ethyl methacrylate, allyl acetate, allyl acrylate, allyl methacrylate, allyl glycidyl ether, vinyl cyclohexene monoepoxide and 4-vinyl styreneoxide, and
      b. starting organohydrogenpolysiloxane represented by the average formula
      $(R)_a(H)_b SiO_{(4-a-b)/2}$
      where R is methyl or phenyl, a and b are each positive numbers expressed as $1 \leq a \leq 2$ and $b \leq 1$, respectively, with the proviso that $2 \leq (a + b) \leq 3$, and having at least two hydrogen atoms directly bonded to the silicon atoms through Si—H linkages in one molecule, in an amount such that the amount of said hydrogen atoms in said starting organohydrogenpolysiloxane is in excess over equimolar to said aliphatic double bond, in the presence of a platinum catalyst, by which part of said Si—H linkages are subjected to addition reaction with said aliphatic double bonds and the remaining of said Si—H linkages are left unreacted,
   B. addition of a compound selected from the group consisting of benzothiazole, 2,2'-dithiobisbenzothiazole, 2-(morpholinothio)benzothiazole, and 2-(morpholinodithio) benzothiazole to the reaction mixture obtained by said partial addition reaction in an amount larger than equimolar to said platinum catalyst, and
   C. recovery of an organohydrogenpolysiloxane as the finished product by distillation.

2. The method for the preparation of an organohydrogenpolysiloxane as claimed in claim 1 wherein said starting organohydrogenpolysiloxane is a cyclic methylhydrogenpolysiloxane with the number of silicon atoms from 3 to 6 in one molecule.

3. The method for the preparation of an organohydrogenpolysiloxane as claimed in claim 1 wherein said starting organohydrogenpolysiloxane is a linear polydimethylsiloxane terminated at both ends by dimethylhydrogensilyl groups.

4. The process of the preparation of an organohydrogenpolysiloxane as claimed in claim 1 wherein said starting organohydrogenpolysiloxane is 1,3,5,7-tetramethylcyclotetrasiloxane.

5. The method for the preparation of an organohydrogenpolysiloxane as claimed in claim 1 wherein said platinum catalyst is selected from the group consisting of chloroplatinic acid, adducts of chloroplatinic acid with alcohols, chloroplatinic acid-olefin complexes, platinum black and finely dispersed platinum supported on alumina or silica carriers.

6. The method for the preparation of an organohydrogenpolysiloxane as claimed in claim 1 wherein said platinum catalyst is employed in an amount ranging from $10^{-7}$ mole to $10^{-3}$ mole per mole of said aliphatic double bonds in said organic unsaturated compound.

* * * * *